(12) United States Patent
Zhong et al.

(10) Patent No.: US 9,433,704 B2
(45) Date of Patent: Sep. 6, 2016

(54) OSTEOSTIMULATIVE SETTABLE BONE GRAFT PUTTY

(75) Inventors: Jipin Zhong, Gainesville, FL (US); David M. Gaisser, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 2342 days.

(21) Appl. No.: 12/074,820

(22) Filed: Mar. 6, 2008

(65) Prior Publication Data

US 2008/0221701 A1 Sep. 11, 2008

Related U.S. Application Data

(60) Provisional application No. 60/906,111, filed on Mar. 9, 2007.

(51) Int. Cl.
| | |
|---|---|
| *A61L 27/42* | (2006.01) |
| *A61F 2/02* | (2006.01) |
| *A61F 2/44* | (2006.01) |
| *A61F 2/46* | (2006.01) |
| *A61F 2/28* | (2006.01) |
| *A61F 2/30* | (2006.01) |

(52) U.S. Cl.
CPC ............ *A61L 27/427* (2013.01); *A61F 2/4644* (2013.01); *A61F 2002/2835* (2013.01); *A61F 2002/30032* (2013.01); *A61F 2002/30062* (2013.01); *A61F 2002/30327* (2013.01); *A61F 2210/0004* (2013.01); *A61F 2250/003* (2013.01); *A61F 2250/0039* (2013.01); *A61F 2310/00329* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,103,002 A | | 7/1978 | Hench et al. |
| 4,775,646 A | | 10/1988 | Hench et al. |
| 4,851,046 A | * | 7/1989 | Low et al. ............... 106/35 |
| 5,281,265 A | | 1/1994 | Liu |
| 5,648,097 A | * | 7/1997 | Nuwayser ............... 424/489 |
| 5,962,549 A | | 10/1999 | Bonfield et al. |
| 6,051,247 A | | 4/2000 | Hench et al. |
| 6,331,312 B1 | | 12/2001 | Lee et al. |
| 6,379,453 B1 | | 4/2002 | Lin et al. |
| 6,423,343 B1 | | 7/2002 | Lee et al. |
| 6,479,565 B1 | | 11/2002 | Stanley |
| 6,663,878 B1 | * | 12/2003 | Greenspan et al. ......... 424/422 |
| 6,733,582 B1 | | 5/2004 | Bohner et al. |
| 7,144,398 B2 | | 12/2006 | Chern Lin et al. |
| 7,275,933 B2 | | 10/2007 | Jia et al. |
| 2002/0098222 A1 | | 7/2002 | Wironen et al. |
| 2004/0254259 A1 | | 12/2004 | Ricci et al. |

OTHER PUBLICATIONS

Portland Cement. http://www.globalspec.com/Specifications/Materials_Chemicals_Adhesives/Industrial_Adhesives/Specialty_Cements_Concretes_Mortars. Archived Aug. 23, 2008. Accessed Oct. 7, 2010.*
Chaumeil. Methods and Findings in Experimental and Clinical Pharmacology. 1998; 20(3): 211-215.*
Huygh. "Microchemical transormation of bioactive glass particles of narrow size range, a 0-24 months study". In: J. Mater. Sci. Mater. Med. Mar. 2002 vol. 13 No. 3 pp. 315-320. Abstract.
Furlaneto. "Bone healing in critical-size defects treated with bioactiveglass/calcium sulfate: a histologic and histometric study in rat calvaria". In: Clin Oral Implants Res. Jun. 2007 vol. 18 No. 3 pp. 311-318. Abstract.
US Food and Drug Administration. 510(k) Summary K051617: NovaBone Putty—Resorbable Bone Void Filler. Retieved from the Internet URL: http://www.fda.gov/cdrh/pdf3/k033994.pdf.
US Food and Drug Administration. 501(k) Summary K033994: NovaBone-BBG—Resorbable Bone Graft Substitute. Retrieved from the Internet URL: http://www.fda.gov/cdrh/pdf3/k033994.pdf.

* cited by examiner

*Primary Examiner* — David J Blanchard
*Assistant Examiner* — Lori K Mattison
(74) *Attorney, Agent, or Firm* — Brinks Gilson & Lione

(57) ABSTRACT

A settable osteostimulative bone graft putty composition having a bioactive glass particulate component composed of a long-term and a short-term component; the long-term component having particle sizes greater than 90 micrometers and the short-term component having particle sizes less than 90 micrometers; the long-term component comprising about 60% to 90% of the bioactive glass osteostimulative particulate component dry weight and the short-term component comprising about 40% to 10%; a binder component having a calcium sulfate component and a calcium silicate component; the calcium sulfate component comprising about 35% to 50% of the binder component dry weight and the calcium silicate component comprising about 65% to 50%; the bioactive glass osteostimulative particulate component being about 20% to 60% of the total putty dry weight composition and the binder being about 80% to 40%; the bioactive glass particulate component and the binder component mixable in water to form the putty.

17 Claims, No Drawings

OSTEOSTIMULATIVE SETTABLE BONE GRAFT PUTTY

This application claims the benefit of U.S. Provisional Patent Application Ser. No. 60/906,111, filed Mar. 9, 2007, the disclosure of which is incorporated herein.

FIELD OF INVENTION

The present invention relates generally to the field of bone graft materials, and more specifically to synthetic bone graft materials that are load-bearing and that actively stimulate bone defect repair while slowly being absorbed from the application site.

BACKGROUND AND DESCRIPTION OF PRIOR ART

In orthopedic, oral and craniofacial surgery, there is often a need for a graft material to repair bone defects originating from disease, surgery, or traumatic injury. The primary bone graft material used consists of human bone tissue collected either from the patient or from a donor. Autogenous bone from the patient has been demonstrated to induce bone growth and defect repair, but its collection generally requires a second surgical site, increasing the risk of complications and recovery time. Allogenic bone from donors or cadavers also is used, but these tissues may result in immunologic reactions and rejection and harbor the potential for disease transmission. Beyond the medical problems associated with these tissue grafts, another problem is tissue graft form. When supplied as a piece of solid bone, these grafts can act as structural grafts to support physiologic loads. However, these grafts are difficult to shape and anchor in place without the use of surgical pins or screws. To overcome this problem, it is known to prepare tissue grafts in a paste or putty form to fill non-uniform defects, but these grafts remain in a soft pliable form and are not load-bearing without the use of other structural surgical hardware such as pins, screws, and bone plates.

Another common problem with tissue grafts is their unpredictable absorption properties. Some tissue grafts may last several years in a site, while otherwise similar tissue grafts may be absorbed within several months. In certain surgical procedures, this absorption rate may result in compromised healing if the graft is absorbed too rapidly. In such cases, very slow absorption and strong mechanical strength are required to maintain long-term mechanical support. An example of such a procedure would be in vertebroplasty surgery, in which a needle is inserted into the center of a collapsed vertebra and a bone replacement material is injected. When the material has filled the bone cavity, it is cured and set, thereby stabilizing the fractured vertebra. As bone growth in such sites is very limited, long term support from the injected material is critical.

Synthetic graft materials, those not involving human and/or animal tissues, also are used for bone defect filling, but primarily as bulk inactive fillers. The main problem with most synthetic materials is that they act solely as passive scaffolds for bone repair and do not stimulate bone formation similar to autogenous bone. Another problem with these materials is that they primarily are in a particulate or paste form, hence they suffer from the same problem as the putty/paste forms of tissue grafts in that they are not load-bearing and require use of other structural hardware. Another drawback associated with many synthetic materials is that they have absorption rates incompatible with bone healing. Some materials such as metals and hydroxyapatite ceramic/cements are permanent replacements and impair healing of the graft site. Other materials such as calcium sulfate ceramics are absorbed by the body at a rate faster than bone formation can occur, leaving a weakened graft site.

One synthetic material has been demonstrated to directly stimulate the cells necessary for bone formation. This material, bioactive glass, is generally composed of the elements silicon, calcium, phosphorus, sodium, and oxygen, although other elements such as boron, potassium, magnesium and fluorine for example, may be added to modify various characteristics, as disclosed in U.S. Pat. Nos. 4,103,002, 4,775,646 and 4,851,046, the disclosure of which is incorporated herein by reference. A representative bioactive glass composition may comprise for example 40 to 52 wt. % $SiO_2$, 10 to 50 wt. % CaO, 10 to 35 wt. % $Na_2O$, 2 to 8 wt. % $P_2O_5$, 0 to 25 wt. % $CaF_2$, 0 to 10 wt. % $B_2O_3$, 0 to 8 wt. % $K_2O$, and 0 to 5 wt. % MgO. As a preferred example, one specific bioactive glass composition, marketed under the brand name BIOGLASS®, has a composition of approximately 21% silicon, 18% calcium, 18% sodium, 3% phosphorus, and 40% oxygen (by weight percent). This BIOGLASS material has been used clinically for over 12 years as a particulate bone graft composition.

Bioactive glass bone grafting compositions have been defined as being osteostimulative, stimulating the function of the osteoblast cells responsible for bone formation. The osteostimulative action of the material is a function of the material composition and its dissolution and absorption characteristics. Upon implantation and contact with body fluids, the bioactive glass particles begin to react, dissolving out sodium, calcium, and phosphorus ions from the surface. The calcium and phosphorus ions redeposit back onto the surfaces of the composition particles, forming a calcium-phosphate layer similar to the hydroxylapatite mineral that makes up the natural mineral phase of bone. Osteoblasts and other proteins in the graft site readily attach to this calcium-phosphate layer, resulting in the rapid osteostimulative bone formation directly in contact with the composition. Over time, the surface dissolution and reactive processes continue until the entire composition is absorbed, leaving behind only the newly formed bone.

One of the drawbacks with bioactive glass bone graft compositions is that they only are available in particulate or non-hardening paste forms, which limits their practical application in load-bearing sites. In addition, the absorption rate of this bioactive glass is such that it may be absorbed prior to complete healing of defects requiring extended healing times, such as in the aforementioned spinal defects or in subjects with compromised and/or delayed healing rates. As with the tissue grafts, a very slow absorption rate and strong mechanical strength are required to maintain long-term mechanical integrity. For these cases, it is desired that the graft material stay active in the graft site for longer than periods than currently achieved to prolong the stimulatory action on the bone.

In these respects, the osteostimulative bone graft putty according to the present invention substantially departs from the conventional concepts and designs of the prior art, and in so doing, provides a composition developed primarily for providing a load-bearing graft material that stimulates bone formation and healing as it is absorbed from the implant site.

In view of the foregoing disadvantages inherent with the known types of graft material present in the prior art, the present invention provides a new bone graft material that can be readily applied to a graft site to support local applied loads and stimulate new bone formation and defect healing.

The general purpose of the present invention, which will be described subsequently in greater detail, is to provide a new bone graft material that has many of the advantages of the graft material mentioned heretofore and many novel features that result in a new bone graft material which is not anticipated, rendered obvious, suggested, or implied by any of the prior are bone graft materials, either alone or in any combination thereof.

In this respect, before explaining at least one embodiment of the invention in detail, it is understood that the invention is not limited in its application to the details of composition or the proportions thereof as set forth in the following description. The invention is capable of other similar embodiments. Also, it is to be understood that the phrasing and terminology employed herein are for the purpose of the description and should not be regarded as limiting.

The primary object of the present invention is to provide a bone graft material that will overcome the shortcomings of prior art compositions.

An object of the present invention is to provide a bone graft material that will set after implantation and act as a load-bearing material.

Another object is to provide a bone graft material that is not permanent and will be absorbed from the graft site.

Another object is to provide a bone graft material that will stimulate bone formation in the graft site immediately upon implantation.

Another object is to provide a bone graft material that will sustain bone stimulation at extended periods after implantation.

Other objects and advantages of the present invention will become obvious to the reader and it is intended that these objects and advantages are within the scope of the present invention. To accomplish the above and related objects, this invention is described in the detailed description presented herewith, attention being called to the fact, however, that the variations to the actual details may be made in the course of final development work.

SUMMARY OF THE INVENTION

The invention is a settable osteostimulative bone graft putty composition and generally comprises an osteostimulative particulate component in combination with a settable binder material. The osteostimulative particulate component consists essentially of a bioactive glass having a controlled composition defined by two different particle size distributions. The settable binder component also consists essentially of a two-component composition, combining a slow-setting material with a more rapid setting material. When mixed with water, saline or the like, the prepared composition is shaped and implanted and hardens in place to support physiologic loading of up to 40 MPa. The osteostimulative particulate stimulates new bone formation and healing and the binder material provides load support until such time as it is ultimately absorbed via normal physiologic processes and replaced with new bone.

The invention may also be summarized as a settable osteostimulative bone graft putty composition consisting essentially of a bioactive glass osteostimulative particulate component consisting essentially of a long-term bioactive glass osteostimulative particulate component characterized by a slow absorption rate in the human body and a short-term bioactive glass osteostimulative particulate component characterized by a faster absorption rate in the human body than said long-term bioactive glass osteostimulative particulate component; and a binder component consisting essentially of a calcium sulfate component characterized by a fast setting time and a calcium silicate component characterized by a slower setting time in comparison to said calcium sulfate component; said bioactive glass osteostimulative particulate component and said binder component mixable in water to form said putty.

The invention may also be summarized as a settable osteostimulative bone graft putty composition consisting essentially of a bioactive glass osteostimulative particulate component consisting essentially of a long-term bioactive glass osteostimulative particulate component and a short-term bioactive glass osteostimulative particulate component; said long-term component having particle sizes of between about 90 to 1000 micrometers and said short-term component having particle sizes of less than about 90 micrometers; said long-term component comprising about 60% to 90% of said bioactive glass osteostimulative particulate component dry weight and said short-term component comprising about 40% to 10% of said bioactive glass osteostimulative particulate component dry weight; and a binder component consisting essentially of a calcium sulfate component and a calcium silicate component; said bioactive glass osteostimulative particulate component and said binder component mixable in water to form said putty.

The invention may also be summarized as a settable osteostimulative bone graft putty composition consisting essentially of a bioactive glass osteostimulative particulate component consisting essentially of a long-term bioactive glass osteostimulative particulate component and a short-term bioactive glass osteostimulative particulate component; said long-term component having particle sizes of between about 120 to 710 micrometers and said short-term component having particle sizes of between about 20 to 50 micrometers; said long-term component comprising about 60% to 90% of said bioactive glass osteostimulative particulate component dry weight and said short-term component comprising about 40% to 10% of said bioactive glass osteostimulative particulate component dry weight; and a binder component consisting essentially of a calcium sulfate component and a calcium silicate component; said calcium sulfate component comprising about 35% to 50% of said binder component dry weight and said calcium silicate component comprising about 65% to 50% of said binder component dry weight; said bioactive glass osteostimulative particulate component comprising about 20% to 60% of the total putty dry weight composition and said binder comprising about 80% to 40% of the total putty dry weight composition; said bioactive glass osteostimulative particulate component and said binder component mixable in water to form said putty.

DETAILED DESCRIPTION OF THE INVENTION

As described herein, the invention comprises a multi-component composition that, when mixed with a suitable fluid, will set and attain a load-bearing capacity after implantation. A preferred embodiment of the invention is a four-component system, with two osteostimulative components and two binder components. The osteostimulative components are further defined as being one short-term component for immediate stimulatory action, and one long-term component for sustained stimulatory action. The binder components are further defined as being one rapid setting binder and one slow setting binder. All components preferably are pre-mixed in powder form, needing only activation upon mixing with a wetting solution.

The long-term osteostimulative component generally consists essentially of bioactive glass particulate. The particulate may be heat treated to at least in part convert the material to a crystalline structure, but this is not required for the efficacy of the invention as disclosed herein. The crystallization of the osteostimulative component acts to stabilize the physical structure of particles without altering their chemical composition, retaining their bioactive capacity while reducing the absorption rate. In addition, varying the particle size of the crystallized osteostimulative component may be utilized to further control absorbability.

The short-term osteostimulative component primarily consists essentially of a bioactive glass particulate having a reduced particle size. The reduced particle size results in a bimodal size distribution of osteostimulative particulate. The particles with the reduced size are more rapidly dissolved on implantation. This dissolution is an inherent function in establishing the osteostimulative function of the material in the immediate post-implantation period.

The quick setting binder component consists essentially of calcium sulfate. On mixing with water, this material reacts to form a rigid material with a compressive strength sufficient to be clinically useful for osseous defect repair. This material is currently in use by itself as a bone graft material, but it has an absorption period of only three to six weeks, making it unsuitable for long-term use on its own.

The slow setting binder component consists essentially of calcium silicate, similar to that used in Portland cement. Generally requiring a longer setting time, these materials are very strong, with compression strengths reaching 40 MPa. Unlike the calcium sulfate, the absorption time of calcium silicates is greatly extended, increasing the life of the graft material and thereby sustaining the osteostimulative components in place for longer periods.

Although other compositions are possible within the scope of this invention, one representative preferred embodiment of the composition is described herewith. The embodiment contains bioactive glass (preferably BIO-GLASS®) osteostimulative particulate components, comprising for example between about 20% and 65% of the total dry weight composition. A more preferred range of the bioactive glass osteostimulative particulate components is between about 20% and 40%, and a most preferred range is between about 25% to 35%. The long-term osteostimulative component particles have a particle size for example generally within the range of about 90 to 1000 micrometers, with a more preferred particle size range being about 90 to 710 micrometers, and a most preferred range being about 120 to 710 micrometers. Most preferably, approximately half of the long-term osteostimulative component particles have a particle size of between 250 and 450 micrometers. The short-term osteostimulative component particles have a particle size for example of less than about 90 micrometers, with a more preferred range of particle size being about 20 to 90 micrometers, and a most preferred range being about 20 to 50 micrometers. In terms of the combined bioactive glass osteostimulative particulate components by dry weight, the long-term component preferably comprises about 60% to 90% and the short-term component comprises about 40% to 10%.

The binder components generally consist essentially for example of between about 35% and 80% of the total composition by dry weight. The quick setting binder component is primarily for example a calcium sulfate, preferably calcium sulfate hemihydrate ($CaSO_4 \cdot 1/2H_2O$), which reacts with water to form calcium sulfate dihydrate ($CaSO_4 \cdot 2H_2O$) upon mixing. The slow setting binder component is primarily for example a calcium silicate, preferably tricalcium silicate $(CaO)_3 \cdot SiO_2$ (or $Ca_3SiO_5$). The composition preferably has a general initial setting or stabilization time of between ten and fifteen minutes to provide stabilization at the time of implantation. In terms of the combined binder components, the quick setting binder component preferably comprises about 35% to 50% and the slow setting binder component comprises about 65% to 50%.

As a functional overview, it is generally intended that the invention be supplied in a pre-mixed dry powder form. Mixed with saline (approximately 0.9% NaCl) or other similar fluid at ambient temperature, preferably in a ratio of approximately 0.3 to 0.4 ml/g, the material forms a manageable damp paste which can be placed into the graft site (e.g., the removal site of a tumor or tooth, internal to a vertebra, etc.) and shaped, at which time it begins to harden, eventually reaching a strength of about 20 to 40 MPa. Osteostimulative component particles exposed at the exterior surfaces of the graft mass begin to directly stimulate the bone healing response. As the composition slowly is absorbed, first upon degradation of the calcium sulfate component and later upon degradation of the calcium silicate component, additional osteostimulative component particles are continually exposed. The smaller short-term particles rapidly dissolve on exposure, further stimulating new bone formation. The long-term particles then continue to act as a stimulative agent over their prolonged duration in the graft site. Eventually all of the binder components are absorbed.

It is understood that equivalents and substitutions to certain elements set forth above may obvious to those skilled in the art, and therefore the true scope and definition of the invention is to be as set forth in the following claims.

We claim:

1. A settable osteostimulative bone graft putty composition consisting essentially of:

a bioactive glass osteostimulative particulate component consisting essentially of a long-term bioactive glass osteostimulative particulate component characterized by a slow absorption rate in the human body and a short-term bioactive glass osteostimulative particulate component characterized by a faster absorption rate in the human body than said long-term bioactive glass osteostimulative particulate component;

said long-term component having particle sizes greater than 90 micrometers and said short-term component having particle sizes of less than 90 micrometers;

said long-term component comprising about 60% to 90% of said bioactive glass osteostimulative particulate component dry weight and said short-term component comprising about 40% to 10% of said bioactive glass osteostimulative particulate component dry weight;

a binder component consisting essentially of a calcium sulfate component characterized by a fast setting time and a calcium silicate component characterized by a slower setting time in comparison to said calcium sulfate component; and water;

said bioactive glass osteostimulative particulate component and said binder component mixable in said water to form said putty, said putty retaining shape and supporting physiologic loading of up to 40 MPa after setting.

2. The composition of claim 1, said long-term component having particle sizes of between about 120 to 710 micrometers and said short-term component having particle sizes of between about 20 to 50 micrometers.

3. The composition of claim 1, said bioactive glass osteostimulative particulate component comprising about 20% to 60% of the total putty dry weight composition and said binder component comprising about 80% to 40% of the total putty dry weight composition.

4. The composition of claim 3, said bioactive glass osteostimulative particulate component comprising about 20% to 40% of the total putty dry weight composition and said binder component comprising about 80% to 60% of the total putty dry weight composition.

5. The composition of claim 4, said bioactive glass osteostimulative particulate component comprising about 25% to 35% of the total putty dry weight composition and said binder component comprising about 75% to 65% of the total putty dry weight composition.

6. The composition of claim 1, said calcium sulfate component comprising about 35% to 50% of said binder component dry weight and said calcium silicate component comprising about 65% to 50% of said binder component dry weight.

7. The composition of claim 1, approximately 50% of said long-term component having particle sizes of between 250 and 450 micrometers.

8. A settable osteostimulative bone graft putty composition consisting essentially of:
   a bioactive glass osteostimulative particulate component consisting essentially of a long-term bioactive glass osteostimulative particulate component and a short-term bioactive glass osteostimulative particulate component;
   said long-term component having particle sizes of between 90 to 1000 micrometers and said short-term component having particle sizes of less than 90 micrometers;
   said long-term component comprising about 60% to 90% of said bioactive glass osteostimulative particulate component dry weight and said short-term component comprising about 40% to 10% of said bioactive glass osteostimulative particulate component dry weight;
   a binder component consisting essentially of a calcium sulfate component and a calcium silicate component; and
   water;
   said bioactive glass osteostimulative particulate component and said binder component mixable in said water to form said putty, said putty retaining shape and supporting physiologic loading of up to 40 MPa after setting.

9. The composition of claim 8, said calcium sulfate component comprising about 35% to 50% of said binder component dry weight and said calcium silicate component comprising about 65% to 50% of said binder component dry weight.

10. The composition of claim 9, said bioactive glass osteostimulative particulate component comprising about 20% to 60% of the total putty dry weight composition and said binder component comprising about 80% to 40% of the total putty dry weight composition.

11. The composition of claim 10, said bioactive glass osteostimulative particulate component comprising about 20% to 40% of the total putty dry weight composition and said binder component comprising about 80% to 60% of the total putty dry weight composition.

12. The composition of claim 11, said bioactive glass osteostimulative particulate component comprising about 25% to 35% of the total putty dry weight composition and said binder component comprising about 75% to 65% of the total putty dry weight composition.

13. The composition of claim 8, said bioactive glass osteostimulative particulate component comprising about 20% to 60% of the total putty dry weight composition and said binder component comprising about 80% to 40% of the total putty dry weight composition.

14. The composition of claim 8, said long-term component having particle sizes of between about 120 to 710 micrometers and said short-term component having particle sizes of between about 20 to 50 micrometers.

15. A settable osteostimulative bone graft putty composition consisting essentially of:
   a bioactive glass osteostimulative particulate component consisting essentially of a long-term bioactive glass osteostimulative particulate component and a short-term bioactive glass osteostimulative particulate component;
   said long-term component having particle sizes of between about 120 to 710 micrometers and said short-term component having particle sizes of between about 20 to 50 micrometers;
   said long-term component comprising about 60% to 90% of said bioactive glass osteostimulative particulate component dry weight and said short-term component comprising about 40% to 10% of said bioactive glass osteostimulative particulate component dry weight;
   a binder component consisting essentially of a calcium sulfate component and a calcium silicate component;
   said calcium sulfate component comprising about 35% to 50% of said binder component dry weight and said calcium silicate component comprising about 65% to 50% of said binder component dry weight;
   said bioactive glass osteostimulative particulate component comprising about 20% to 60% of the total putty dry weight composition and said binder component comprising about 80% to 40% of the total putty dry weight composition; and
   water;
   said bioactive glass osteostimulative particulate component and said binder component mixable in said water to form said putty, said putty retaining shape and supporting physiologic loading of up to 40 MPa after setting.

16. The composition of claim 15, said bioactive glass osteostimulative particulate component comprising about 25% to 35% of the total putty dry weight composition and said binder component comprising about 75% to 65% of the total putty dry weight composition.

17. The composition of claim 15, approximately 50% of said long-term component having particle sizes of between 250 and 450 micrometers.

* * * * *